US009289243B2

(12) United States Patent
Dekutoski et al.

(10) Patent No.: US 9,289,243 B2
(45) Date of Patent: Mar. 22, 2016

(54) METHODS FOR CORRECTING SPINAL DEFORMITIES

(71) Applicant: WARSAW ORTHOPEDIC, INC., Warsaw, IN (US)

(72) Inventors: Mark Benedict Dekutoski, Rochester, MN (US); John Durward Pond, Jr., Germantown, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 0 days.

(21) Appl. No.: 14/286,563

(22) Filed: May 23, 2014

(65) Prior Publication Data

US 2014/0257404 A1     Sep. 11, 2014

Related U.S. Application Data

(63) Continuation of application No. 11/739,919, filed on Apr. 25, 2007, now abandoned.

(51) Int. Cl.
*A61B 17/70*     (2006.01)
*A61B 17/56*     (2006.01)

(52) U.S. Cl.
CPC ......... *A61B 17/7011* (2013.01); *A61B 17/7004* (2013.01); *A61B 17/7083* (2013.01); *A61B 2017/564* (2013.01)

(58) Field of Classification Search
CPC ............ A61B 17/7032; A61B 17/7001; A61F 2/4611
USPC ....................................................... 606/279
See application file for complete search history.

(56) References Cited

U.S. PATENT DOCUMENTS

| 4,078,559 A | 3/1978 | Nissinen |
| 4,112,935 A | 9/1978 | Latypov et al. |

(Continued)

FOREIGN PATENT DOCUMENTS

| EP | 0470660 A | 2/1992 |
| WO | 2006104538 A1 | 10/2006 |

(Continued)

OTHER PUBLICATIONS

Labelle, H., et al., "Peroperative Three-Dimensional Correction of Idiopathic Scoliosis with the Cotrel-Dubousset Procedure". Spine, vol. 20, No. 12, pp. 1406-1409. 1995.

(Continued)

*Primary Examiner* — Todd E Manahan
*Assistant Examiner* — Juilanna N Harvey

(57) ABSTRACT

The present application discloses methods for treating spinal deformities. One embodiment includes inserting an elongated corrective member into the patient. During insertion, the corrective member is operatively attached to a first vertebral member that applies a first corrective force to correct a first vertebral member alignment. The corrective member is further inserted into the patient and subsequently operatively attached to a second vertebral member that applies a second corrective force to correct a second vertebral member alignment. The corrective member is further inserted and subsequently operatively attached to a third vertebral member that applies a third corrective force to correct a third vertebral member alignment. The embodiment may further include operatively attaching the corrective member to additional vertebral members to correct further misalignment. In one embodiment, a second member is attached to the vertebral members after they have been aligned to maintain the alignment.

18 Claims, 11 Drawing Sheets

(56) References Cited

U.S. PATENT DOCUMENTS

| | | | |
|---|---|---|---|
| 4,274,401 A | 6/1981 | Miskew | |
| 4,361,141 A | 11/1982 | Tanner | |
| 4,409,968 A | 10/1983 | Drummond | |
| 4,505,268 A | 3/1985 | Sgandurra | |
| 4,854,304 A | 8/1989 | Zielke | |
| 5,102,412 A | 4/1992 | Rogozinski | |
| 5,217,461 A | 6/1993 | Asher et al. | |
| 5,219,349 A | 6/1993 | Krag et al. | |
| 5,261,908 A | 11/1993 | Campbell, Jr. | |
| 5,281,223 A | 1/1994 | Ray | |
| 5,282,863 A | 2/1994 | Burton | |
| 5,290,289 A | 3/1994 | Sanders et al. | |
| 5,360,429 A | 11/1994 | Jeanson et al. | |
| 5,425,732 A | 6/1995 | Ulrich | |
| 5,478,340 A | 12/1995 | Kluger | |
| 5,531,747 A | 7/1996 | Ray | |
| 5,540,689 A | 7/1996 | Sanders et al. | |
| 5,586,983 A | 12/1996 | Sanders et al. | |
| 5,591,165 A | 1/1997 | Jackson | |
| 5,591,167 A | 1/1997 | Laurain et al. | |
| 5,593,408 A | 1/1997 | Gayet et al. | |
| 5,603,714 A | 2/1997 | Kaneda et al. | |
| 5,607,425 A | 3/1997 | Rogozinski | |
| 5,658,286 A | 8/1997 | Sava | |
| 5,672,175 A | 9/1997 | Martin | |
| 5,672,176 A * | 9/1997 | Biedermann et al. | 606/271 |
| 5,702,392 A | 12/1997 | Wu et al. | |
| 5,720,751 A | 2/1998 | Jackson | |
| 5,797,910 A | 8/1998 | Martin | |
| 5,944,720 A | 8/1999 | Lipton | |
| 5,951,553 A | 9/1999 | Betz et al. | |
| 5,951,555 A | 9/1999 | Rehak et al. | |
| 6,099,528 A | 8/2000 | Saurat | |
| 6,102,912 A | 8/2000 | Cazin et al. | |
| 6,214,004 B1 | 4/2001 | Coker | |
| 6,287,308 B1 | 9/2001 | Betz et al. | |
| 6,293,949 B1 | 9/2001 | Justis et al. | |
| 6,296,643 B1 | 10/2001 | Hopf et al. | |
| 6,299,613 B1 | 10/2001 | Ogilvie et al. | |
| 6,325,805 B1 | 12/2001 | Ogilvie et al. | |
| 6,458,131 B1 | 10/2002 | Ray | |
| 6,551,320 B2 | 4/2003 | Lieberman | |
| 6,551,329 B1 | 4/2003 | Kortenbach et al. | |
| 6,554,831 B1 | 4/2003 | Rivard | |
| 6,565,568 B1 | 5/2003 | Rogozinski | |
| 6,616,669 B2 | 9/2003 | Ogilvie et al. | |
| 6,623,484 B2 | 9/2003 | Betz et al. | |
| 6,648,888 B1 | 11/2003 | Shluzas | |
| 6,761,719 B2 | 7/2004 | Justis et al. | |
| 6,770,075 B2 | 8/2004 | Howland | |
| 6,773,437 B2 | 8/2004 | Ogilvie et al. | |
| 6,790,209 B2 | 9/2004 | Beale et al. | |
| 6,802,844 B2 | 10/2004 | Ferree | |
| 6,805,716 B2 | 10/2004 | Ralph et al. | |
| 6,837,904 B2 | 1/2005 | Ralph et al. | |
| 6,964,665 B2 | 11/2005 | Thomas et al. | |
| 6,986,771 B2 | 1/2006 | Paul et al. | |
| 6,989,011 B2 | 1/2006 | Paul et al. | |
| 7,052,497 B2 | 5/2006 | Sherman et al. | |
| 7,094,240 B2 | 8/2006 | Molz, IV et al. | |
| 2001/0029375 A1* | 10/2001 | Betz | A61B 17/8095 606/279 |
| 2002/0138077 A1 | 9/2002 | Ferree | |
| 2002/0151895 A1 | 10/2002 | Soboleski et al. | |
| 2003/0060824 A1 | 3/2003 | Viart et al. | |
| 2003/0088251 A1 | 5/2003 | Braun et al. | |
| 2003/0171749 A1 | 9/2003 | Le Couedic et al. | |
| 2003/0191470 A1 | 10/2003 | Ritland | |
| 2004/0052676 A1 | 3/2004 | Wu | |
| 2004/0099356 A1 | 5/2004 | Wu | |
| 2004/0106921 A1 | 6/2004 | Cheung et al. | |
| 2004/0138662 A1 | 7/2004 | Landry et al. | |
| 2004/0172022 A1 | 9/2004 | Landry et al. | |
| 2004/0186472 A1* | 9/2004 | Lewis et al. | 606/61 |
| 2004/0215191 A1 | 10/2004 | Kitchen | |
| 2004/0241037 A1 | 12/2004 | Wu | |
| 2005/0033291 A1 | 2/2005 | Ebara | |
| 2005/0033295 A1 | 2/2005 | Wisnewski | |
| 2005/0055096 A1* | 3/2005 | Serhan | A61F 2/08 623/17.11 |
| 2005/0070917 A1 | 3/2005 | Justis | |
| 2005/0131405 A1 | 6/2005 | Molz, IV et al. | |
| 2005/0143823 A1 | 6/2005 | Boyd et al. | |
| 2005/0171539 A1 | 8/2005 | Braun et al. | |
| 2005/0192581 A1 | 9/2005 | Molz et al. | |
| 2005/0203511 A1 | 9/2005 | Wilson-MacDonald et al. | |
| 2005/0203517 A1 | 9/2005 | Jahng et al. | |
| 2005/0216004 A1 | 9/2005 | Schwab | |
| 2005/0261686 A1 | 11/2005 | Paul | |
| 2005/0277934 A1 | 12/2005 | Vardiman | |
| 2005/0288672 A1 | 12/2005 | Ferree | |
| 2006/0009767 A1 | 1/2006 | Kiester | |
| 2006/0036246 A1 | 2/2006 | Carl et al. | |
| 2006/0074448 A1 | 4/2006 | Harrison et al. | |
| 2006/0155279 A1 | 7/2006 | Ogilvie | |
| 2006/0167459 A1 | 7/2006 | Groiso | |
| 2006/0184178 A1 | 8/2006 | Jackson | |
| 2006/0189985 A1 | 8/2006 | Lewis | |
| 2006/0189986 A1 | 8/2006 | Sherman et al. | |
| 2006/0195090 A1 | 8/2006 | Suddaby | |
| 2006/0195093 A1 | 8/2006 | Jahng | |
| 2006/0200137 A1 | 9/2006 | Soboleski et al. | |
| 2006/0217712 A1 | 9/2006 | Mueller et al. | |
| 2006/0229615 A1 | 10/2006 | Abdou | |
| 2006/0241594 A1 | 10/2006 | McCarthy et al. | |
| 2006/0247658 A1 | 11/2006 | Pond, Jr. et al. | |
| 2006/0271050 A1 | 11/2006 | Piza Vallespir | |
| 2006/0282073 A1 | 12/2006 | Simanovsky | |
| 2007/0162007 A1 | 7/2007 | Shoham | |
| 2007/0173828 A1 | 7/2007 | Firkins et al. | |
| 2007/0213714 A1* | 9/2007 | Justis | A61B 17/7002 606/86 A |
| 2009/0088803 A1 | 4/2009 | Justis et al. | |
| 2010/0185242 A1 | 7/2010 | Barry et al. | |

FOREIGN PATENT DOCUMENTS

| | | |
|---|---|---|
| WO | 2006119447 A1 | 11/2006 |
| WO | 2007045892 A | 4/2007 |

OTHER PUBLICATIONS

Mazda, K, et al., "Efficacy and safety of posteromedial translation for correction of thoracic curves in adolescent idiopathic scoliosis using a new connection to the spine: the Universal Clamp". European Spine Journal. vol. 18, No. 2, pp. 158-169. 2009.

De Jonge, T., et al., "Sagittal plane correction in idiopathic scoliosis." Spine, vol. 27, No. 7, pp. 754-760. Apr. 2002.

Gardner-Morse, M., et al., "Three-dimensional simulations of the scoliosis derotation maneuver with CotrelDubousset instrumentation". Journal of Biomechanics, Vo. 27, No. 2, pp. 177-181. Feb. 1994.

Sengupta, D.K., et al., "Scoliosis—The current concepts." Indian Journal of Orthopaedics, vol. 44, No. 1, pp. 5-8. 2010.

Webb, J.K, et al., "Posterior instrumentation in scoliosis." European Spine Journal, vol. 4, No. 1, pp. 2-5. 1995.

Ghanem, I.B., et al., "Intraoperative optoelectronic analysis of three-dimensional vertebral displacement after Cotrel-Dubousset rod rotation. A preliminary report." Spine, vol. 22, No. 16, pp. 1913-1921. Aug. 1997.

Delorme, S., et al., "Intraoperative comparison of two instrumentation techniques for the correction of adolescent idiopathic scoliosis. Rod rotation and translation." Spine, vol. 24, No. 19, pp. 2011-2017. Oct. 1999.

Suk, S.I., et al., "Is anterior release necessary in severe scoliosis treated by posterior segmental pedicle screw fixation?" European Spine Journal, vol. 16, pp. 1359-1365. 2007.

Maruyama, T., et al., "Surgical treatment of scoliosis: a review of techniques currently applied." Scoliosis, 2008. Biomed Central Ltd.

* cited by examiner

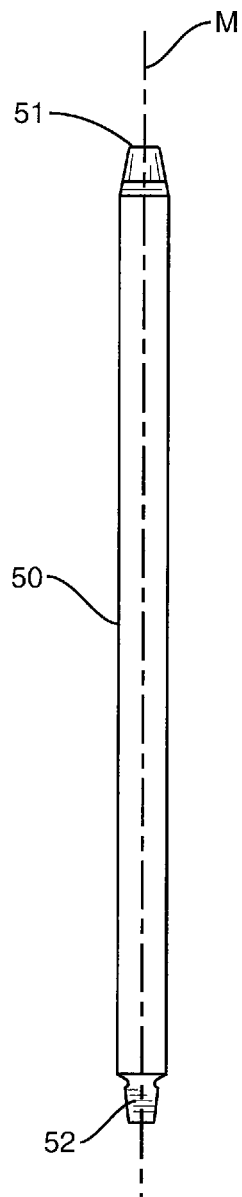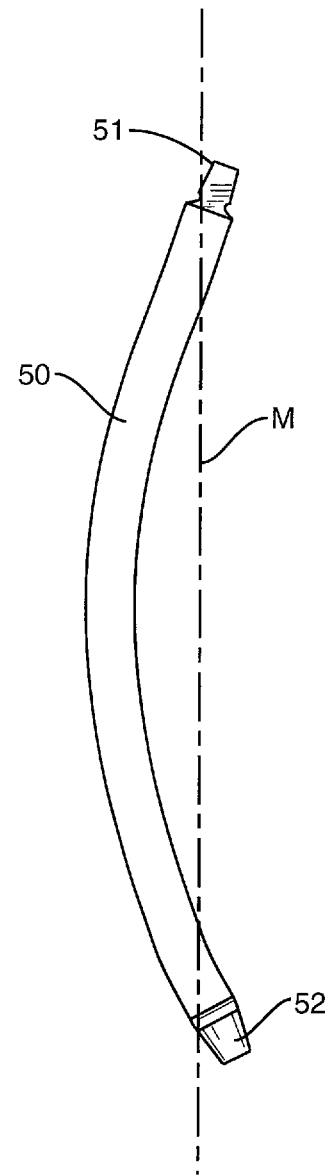
FIG. 7A　　　　　FIG. 7B

METHODS FOR CORRECTING SPINAL DEFORMITIES

CROSS-REFERENCE TO RELATED APPLICATION

This application is a continuation of application Ser. No. 11/739,919, filed on Apr. 25, 2007, the contents of which is herein incorporated by reference, in its entirety.

BACKGROUND

The present application is directed to methods for correcting spinal deformities and, more particularly, to methods of applying a corrective force to one or more of the vertebral members.

The spine is divided into four regions comprising the cervical, thoracic, lumbar, and sacrococcygeal regions. The cervical region includes the top seven vertebral members identified as C1-C7. The thoracic region includes the next twelve vertebral members identified as T1-T12. The lumbar region includes five vertebral members L1-L5. The sacrococcygeal region includes nine fused vertebral members that form the sacrum and the coccyx. The vertebral members of the spine are aligned in a curved configuration that includes a cervical curve, thoracic curve, and lumbosacral curve. Intervertebral discs are positioned between the vertebral members and permit flexion, extension, lateral bending, and rotation.

Various deformities may affect the normal alignment and curvature of the vertebral members. Scoliosis is one example of a deformity of the spine in the coronal plane, in the form of an abnormal curvature. While a normal spine presents essentially a straight line in the coronal plane, a scoliotic spine can present various lateral curvatures in the coronal plane. The types of scoliotic deformities include thoracic, thoracolumbar, lumbar or can constitute a double curve in both the thoracic and lumbar regions. Scoliosis may also include abnormal translation and rotation in the axial and sagittal planes. Schuermann's kyphosis is another example of a spinal deformity that affects the normal alignment of the vertebral members in one or more planes. Further, a fracture of one or more of the vertebral members may cause misalignment along the spine. The term "deformity" and the like is used herein to describe the various types of spinal misalignment.

SUMMARY

The present application discloses methods for treating spinal deformities. One embodiment of a method includes inserting a longitudinal corrective member into the patient. During insertion, the corrective member is operatively attached to a first vertebral member that applies a first corrective force to correct a first vertebral member alignment. The corrective member is further inserted into the patient and subsequently operatively attached to a second vertebral member that applies a second corrective force to correct a second vertebral member alignment. The corrective member is further inserted and subsequently operatively attached to a third vertebral member that applies a third corrective force to correct a third vertebral member alignment. The embodiment may further include operatively attaching the corrective member to additional vertebral members to correct further misalignment. In one embodiment, a second member is attached to the vertebral members after they have been aligned to maintain the alignment.

BRIEF DESCRIPTION OF THE DRAWINGS

FIG. 7A is a top view of a corrective rod in a first rotational position according to one embodiment.

FIG. 7B is a top view of a corrective rod in a second rotational position according to one embodiment.

DETAILED DESCRIPTION

The present application is directed to methods for correcting a spinal deformity. One embodiment of the method includes initially attaching anchors to the vertebral members positioned along a length of a deformed spine. The anchors are positioned along the deformed spine in a first lateral row. An elongated corrective member is than inserted into the patient and through each of the anchors sequentially along the deformed spine. The corrective member is manipulated sequentially to move the vertebral members into alignment. The shape of the corrective member and the movement to fit within the anchors produces a corrective force. This movement sequentially translates the vertebral members at the various spinal levels to treat the spinal deformity. In one embodiment, a second member is inserted into the patient through a second lateral row of anchors. The second rod is secured to the anchors thus causing the vertebral members to remain in the aligned position.

Figure 1:
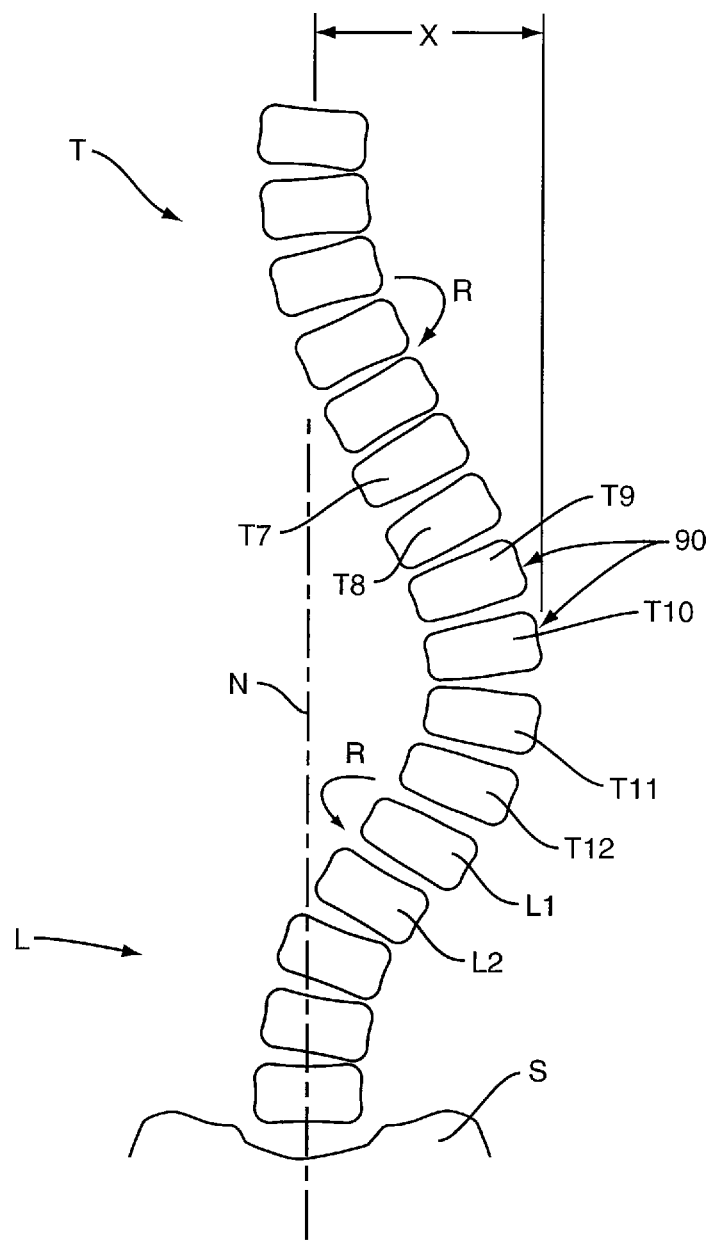
FIG. 1 is a schematic coronal view of an example of a scoliotic spine.

FIG. 1 illustrates a patient's spine that includes a portion of the thoracic region T, the lumbar region L, and the sacrum S. This spine has a scoliotic curve with an apex of the curve being offset a distance X from its correct alignment N in the coronal plane. The spine is deformed laterally and rotationally so that the axes of the vertebral members 90 are displaced from the sagittal plane passing through a centerline of the patient. In the area of the lateral deformity, each of the vertebral members 90 includes a concave side and a convex side. One or more of the vertebral members 90 may be further misaligned due to rotation as depicted by the arrows R. As a result, the axis of the vertebral members 90 which are normally aligned along the coronal plane are non-coplanar and extend along multiple planes.

Figure 2:
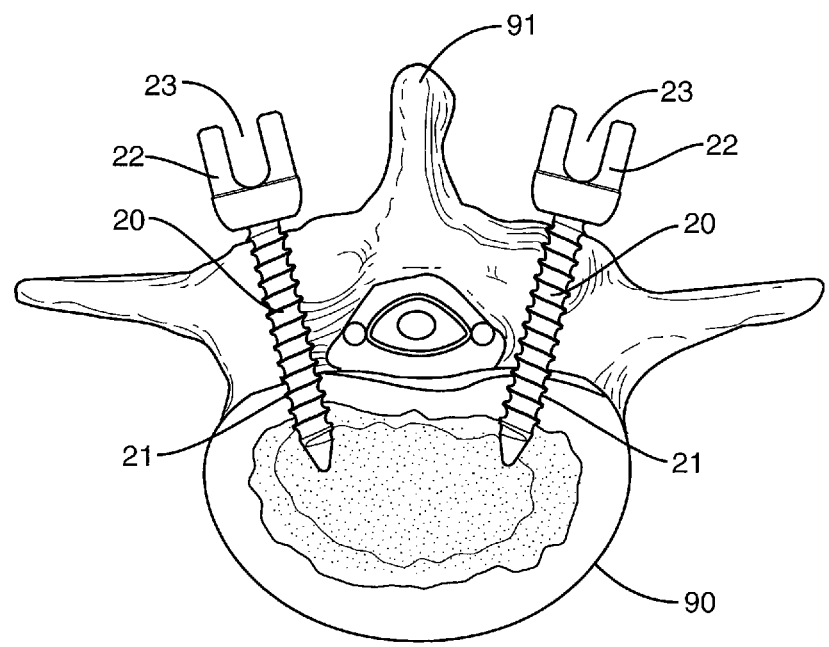
FIG. 2 is a sectional view in the axial plane of a pair of anchors attached to a vertebral member according to one embodiment.

Correction of the spinal deformity initially requires placing anchors within the vertebral members 90. FIG. 2 illustrates one embodiment that includes anchors 20 within the pedicles of the vertebral member 90. The anchors 20 are positioned on each lateral side of the spinous process 91 and include a shaft 21 that extends into the vertebral member 90, and a head 22 positioned on the exterior. Head 22 may be fixedly connected to the shaft 21, or provide movement in one or more planes. Head 22 further includes a receiver 23 to receive a rod as will be explained in detail below. A set screw (not illustrated) is sized to engage with the head 22 to capture the rod within the receiver 23.

In one embodiment, a pair of anchors 20 is positioned within each of the vertebral members 90 along the deformed section of the spine. In another embodiment, a single anchor 20 is positioned within one or more of the vertebral members 90. The single anchor 20 is positioned within either pedicle location.

Figure 3:
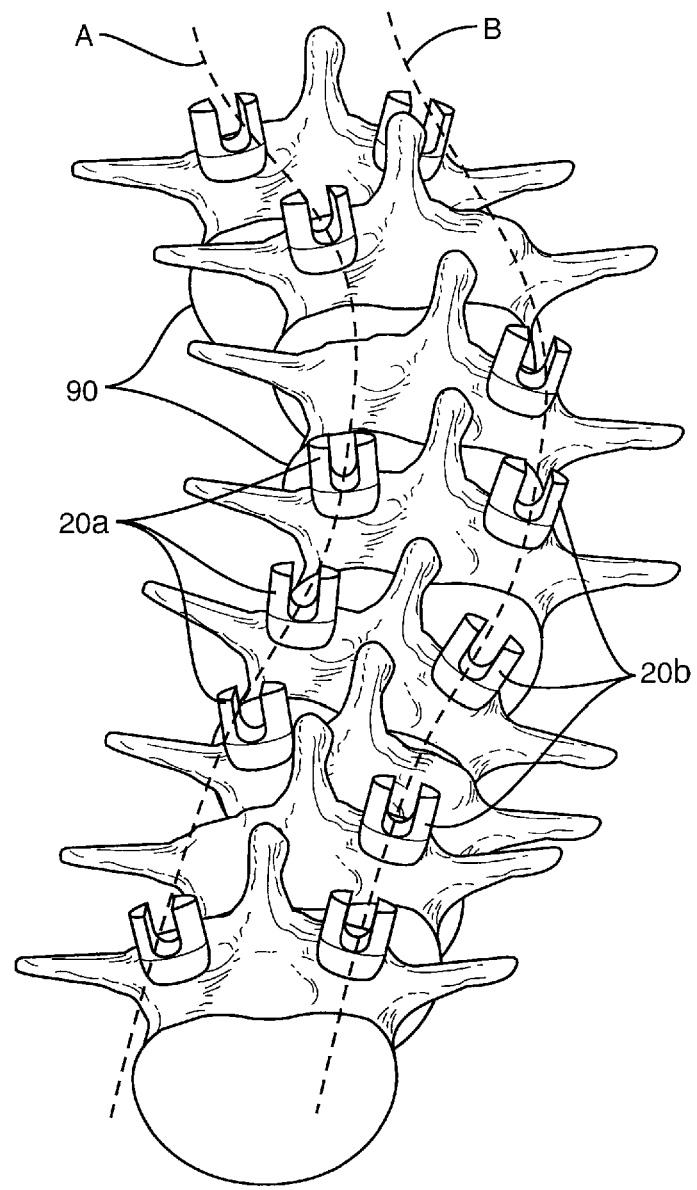
FIG. 3 is a schematic view of anchors attached to the vertebral members along a section of the spine according to one embodiment.

FIG. 3 schematically illustrates the vertebral members 90 that form the deformed spine. One or more anchors 20 are mounted to vertebral members 90 along a section of the spine. In one embodiment as illustrated in FIG. 3, each of the vertebral members 90 includes at least one anchor 20. In another embodiment, one or more of the vertebral members 90 does not include anchors 20. The anchors 20 are arranged to form first and second rows A, B. The first row A is formed by anchors 20a positioned at a first lateral position of the vertebral members 90. Each anchor 20a is positioned at substantially the same lateral position within the respective vertebral member 90. Second row B is formed by anchors 20b positioned at a second lateral position. Likewise, each anchor 20b is positioned at substantially the same lateral position within each vertebral member 90. In one embodiment, rows A and B extend along the spine in a substantially parallel manner.

Figure 4:
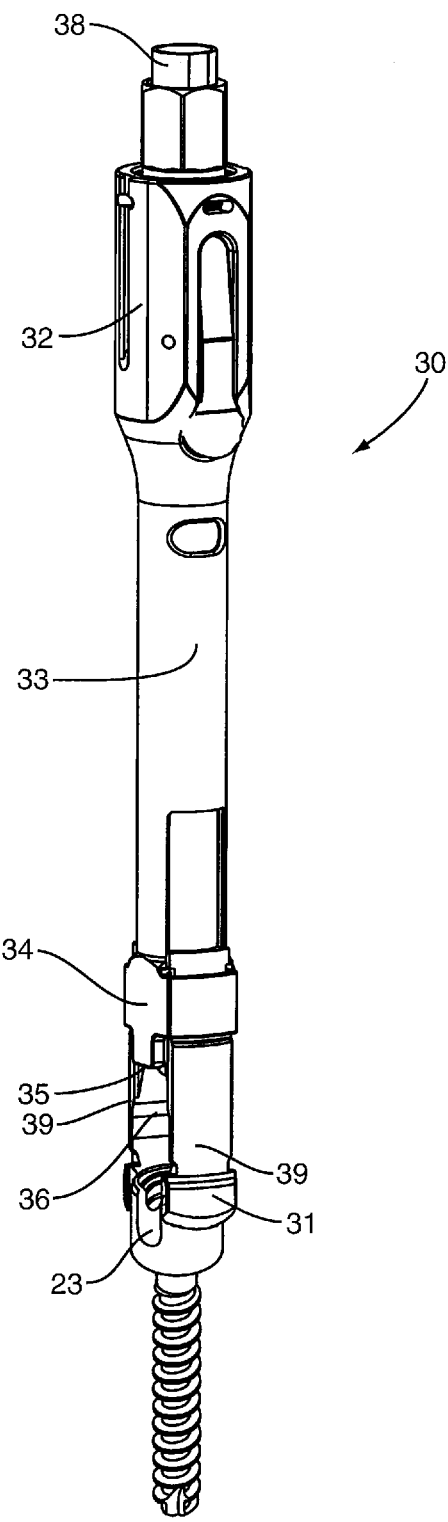
FIG. 4 is a perspective view of an extender in an open orientation and attached to an anchor according to one embodiment.

An extender 30 may be connected to one or more of the anchors 20 along one of the rows A, B. The extenders 30 may function both as a reduction device, as well as a translation and rotation device as will be described in detail below. FIG. 4 illustrates one embodiment of an extender 30 attached to an anchor 20. Extender 30 includes a tubular element 33 with a distal end 31 and a proximal end 32. The tubular element 33 includes a length such that the proximal end 32 extends outward from the patient when the distal end 31 is mounted to the anchor 20.

The distal end 31 includes a pair of opposing legs 39 that connect to the head of the anchor 20. The legs 39 form an opening that aligns with the receiver 23 to form a window 36. The distal end 31 may further include threads adapted for threading engagement with a corresponding portion of the bone anchor 20, or to an element coupled to one or more bone anchors 20. The threads couple the extender 30 to the anchor 20. In a specific embodiment, the threads are engaged with a threaded projection associated with a bone screw, such as, for example, an externally threaded nut used with a pedicle screw. One embodiment of a pedicle screw is used in association with the CD-Horizon Legacy Spinal System manufactured by Medtronic Sofamor Danek of Memphis, Tenn.

A sliding member 34 is movably positioned on the exterior of the tubular element 33 and located in proximity to the distal end 31. Sliding element 34 includes contact edges 35 that form an upper edge of the window 36. The proximal end 32 includes a fitting 38 that is operatively connected to the sliding element 34. Rotation of the fitting 38 in first and second directions causes the sliding element 34 to move downward and upward respectively along the tubular element 33. One example of an extender 30 is the Sextant Perc Trauma Extender available from Medtronic Sofamor Danek of Memphis, Tenn.

Figure 5:
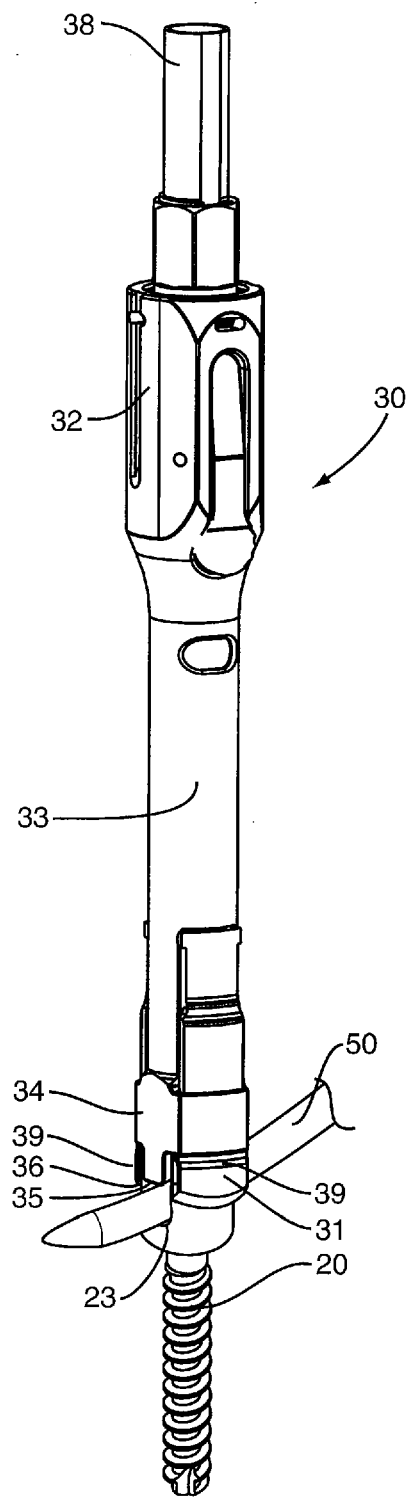
FIG. 5 is a perspective view of an extender in a closed orientation and attached to an anchor according to one embodiment.

FIG. 4 illustrates the extender 30 in an open orientation with the sliding element 34 positioned towards an intermediate section of the tubular element 33. The open orientation gives the window 36 an enlarged size. FIG. 5 illustrates the extender 30 in a closed orientation with the sliding element 34 positioned towards the distal end 31. Movement between the open and closed orientations is caused by rotation of the fitting 38.

Figure 6:
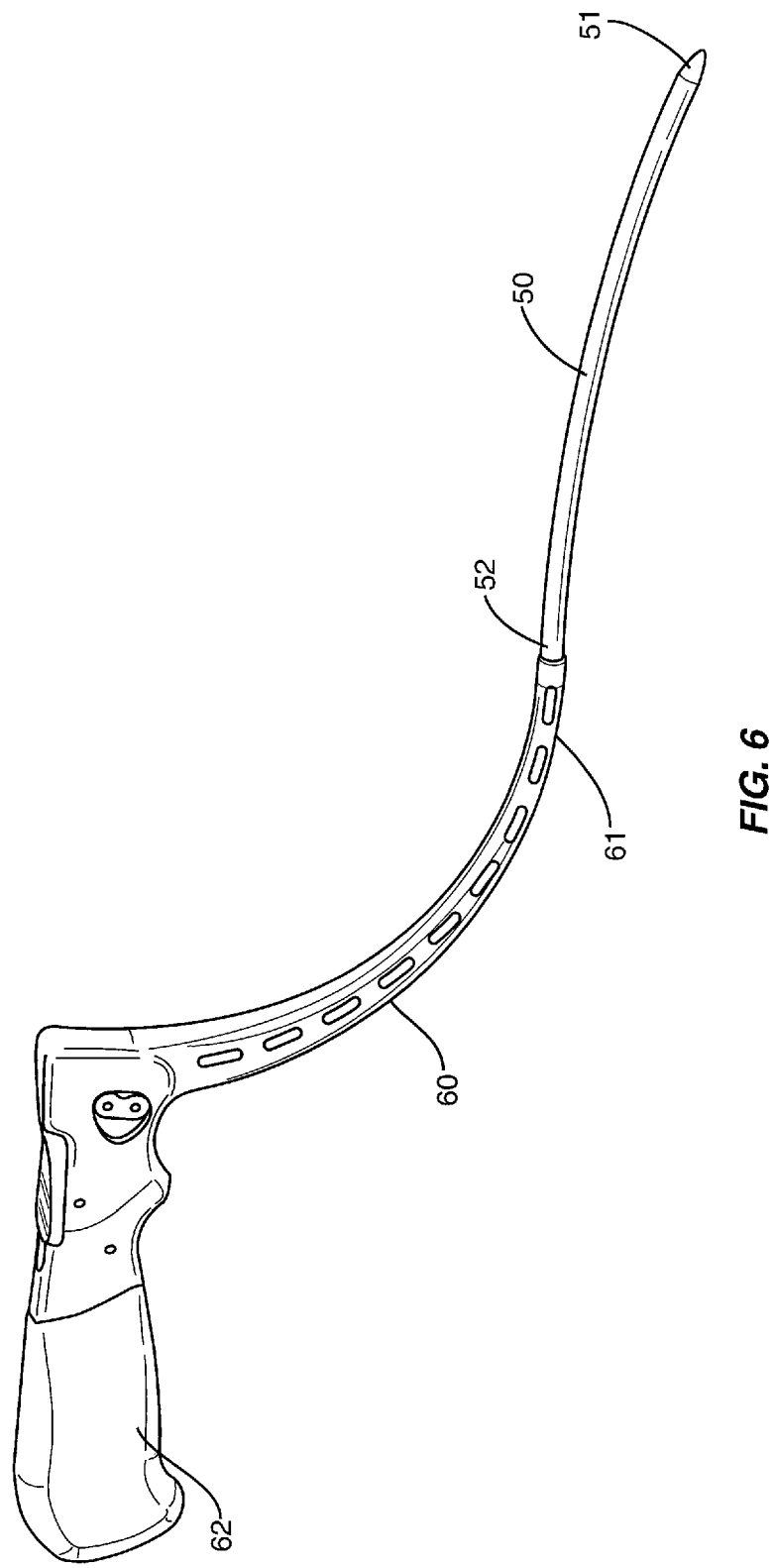
FIG. 6 is a perspective view of a corrective rod and a handle according to one embodiment.

A corrective rod 50 is then sequentially inserted along the spine and attached to the anchors 20 at the various spinal levels. The corrective rod 50 may be inserted in a top-to-bottom direction or a bottom-to-top direction. FIG. 6 illustrates one embodiment of the corrective rod 50 attached to an inserter 60. The corrective rod 50 includes an elongated shape with a tip 51 and a second end 52. In one embodiment, the tip 51 may be sharpened to facilitate insertion and movement through the patient. The length of the rod 50 may vary depending upon the length of the deformed spinal segment to be corrected. As illustrated in FIGS. 7A and 7B, the ends 51, 52 may include a locking aspect to attach with the inserter 60. In one embodiment, the locking aspect includes one or more flat sections and a narrow neck section. These sections maintain the orientation of the corrective rod 50 relative to the inserter 60 during insertion and rotation.

The corrective rod 50 includes a pre-bent shape to apply specific corrective forces to the individual vertebral members 90. In one embodiment, the shape of the corrective rod 50 is determined by studying the flexibility of the spinal deformity prior to the procedure. The shape of the rod 50 corresponds to the needed displacement to translate and/or rotate the vertebral members 90 into alignment. A greater amount of bend at the tip 51 allows for a greater amount of translation and rotation of the vertebral members 90. Rod 50 may be bent in one, two, or three dimensions depending on the amount of correction needed for the vertebral members 90 in the coronal, sagittal, and axial planes.

The curvature of the rod 50 may be more pronounced within a first plane than in a second plane. FIG. 7A illustrates an elevational view of the rod 50 along a first rotational plane. Rod 50 is substantially straight with a line M extending through the tip 51 and the second end 52. This orientation may be used for initial insertion of the rod 50 into the patient. FIG. 7B illustrates the rod 50 in a second rotational plane. The rod 50 is curved away from the line M. This curvature applies a corrective force as will be explained below. In one embodiment, the first plane is offset by about 90 degrees from the second plane.

The corrective rod 50 may be attached to an inserter 60 for insertion and positioning within the patient. As illustrated in FIG. 6, inserter 60 includes a neck 61 with a curved shape for percutaneously inserting the rod 50 into the patient. A handle 62 may be positioned at the end of the neck 61. Handle 62 is sized for grasping and manipulating by the surgeon.

Figure 8:
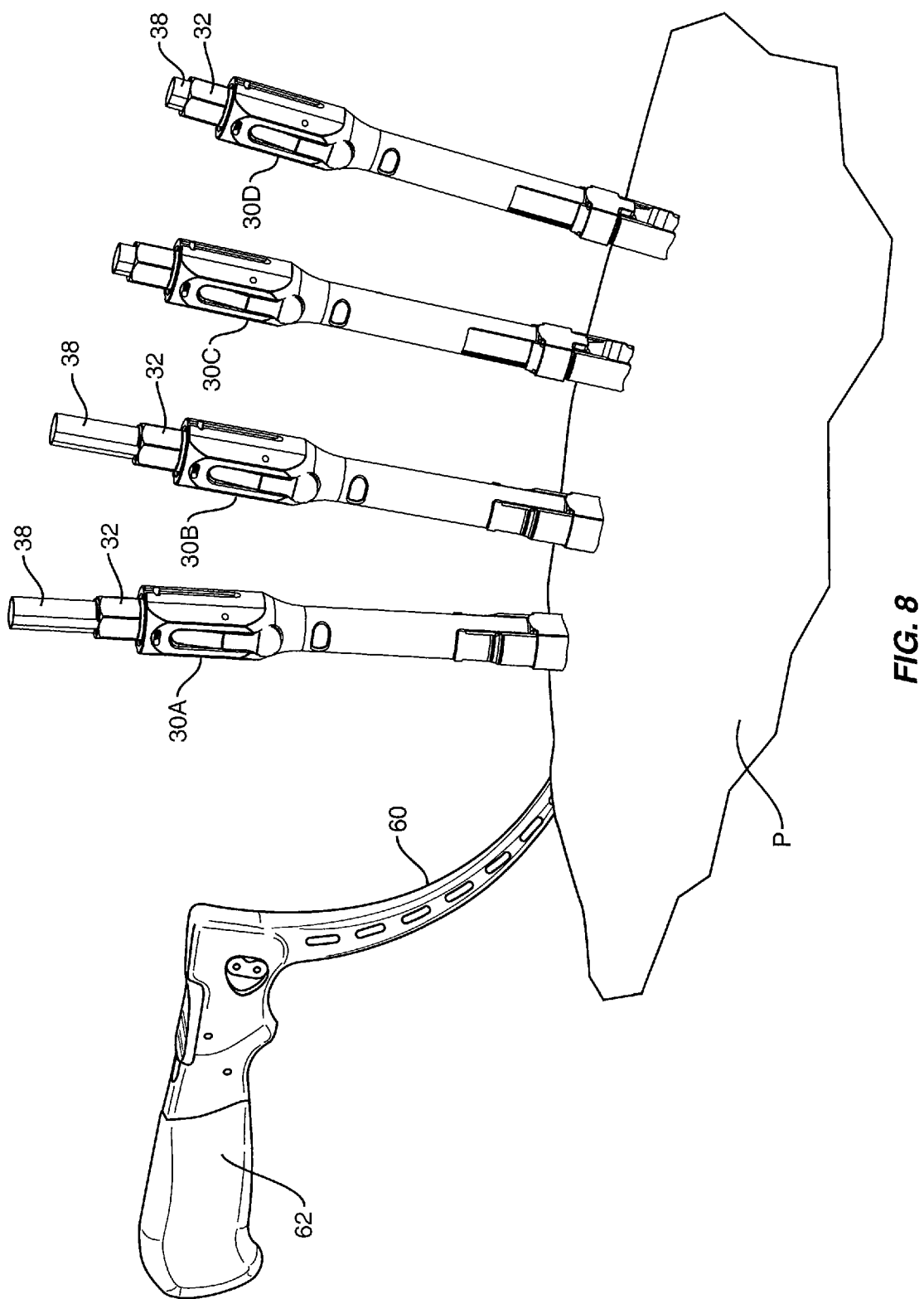
FIG. 8 is a perspective view of a corrective rod in a first rotational position being inserted percutaneously into a patient according to one embodiment.
Figure 9:
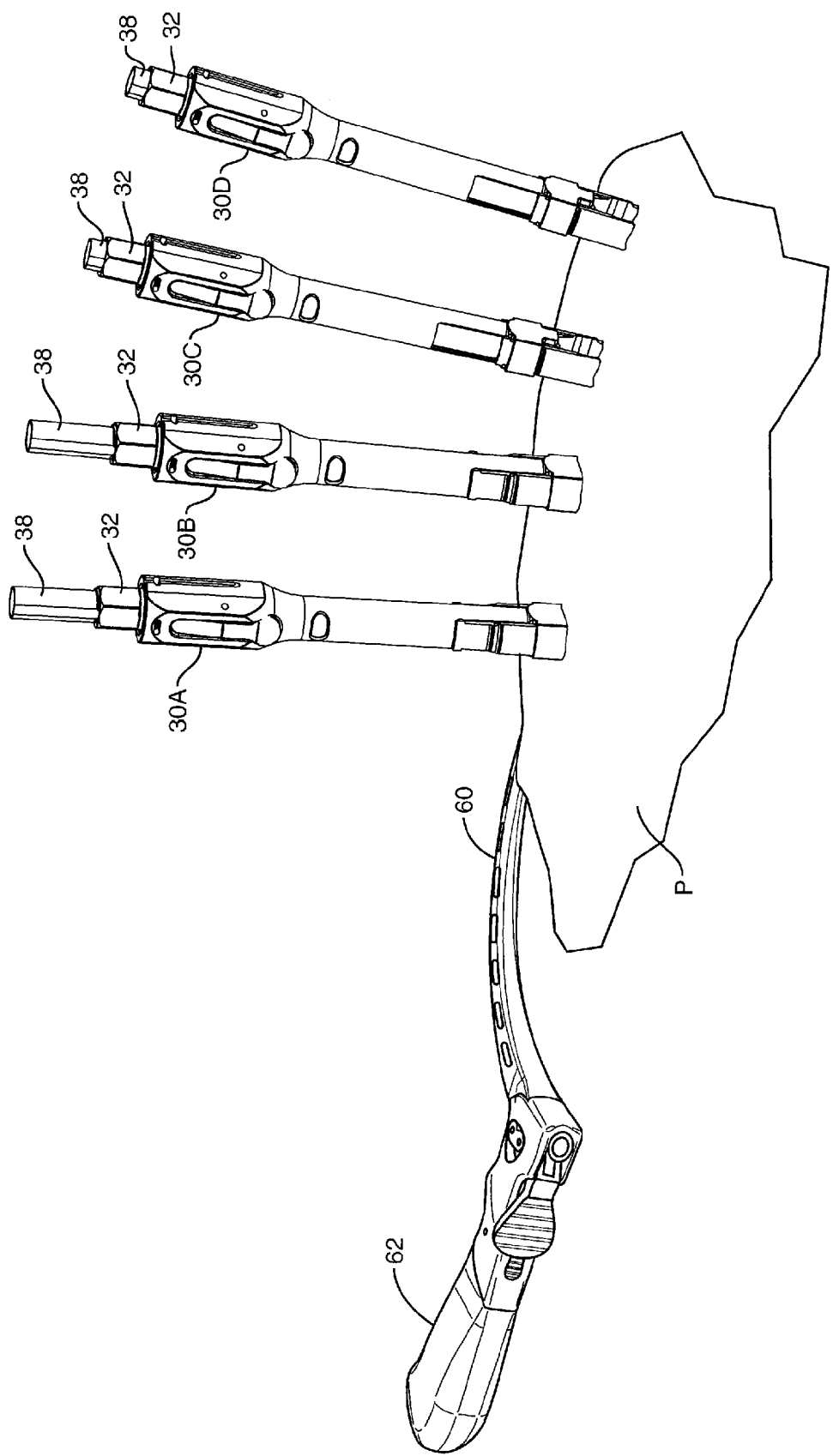
FIG. 9 is a perspective view of a corrective rod inserted within a patient and in a second rotational position according to one embodiment.

The corrective rod 50 is inserted into the patient P as illustrated in FIG. 8. The insertion begins with inserting the tip 51 into the patient and through a first anchor 20 attached to a first vertebral member 90. In the embodiment of FIG. 8, the tip 51 is moved through a first window formed by the first anchor and first extender 30A. After moving through the window, the corrective rod 50 is further inserted into the patient. Insertion into a second window formed by the second anchor and extender 30B at a second vertebral member 90 may require the rod 50 to be rotated and laterally moved relative to the vertebral members 90 because the curvature of the spine causes the second anchor 20 to be misaligned with the first anchor 20. The rotation and lateral movement of the rod 50 during the insertion applies a force to translate and/or rotate the second vertebral member 90 into alignment with the first vertebral member 90. FIG. 9 illustrates the handle 60 and corrective rod 50 being rotated approximately 90° relative to the position in FIG. 9.

This process continues as the tip 51 is moved sequentially through a third window formed at the third extender 30C, and through a fourth window formed at the fourth extender 30D. The insertion of the tip 51 into each window and the accompanying rotation of the corrective rod 50 applies a corrective force to that vertebral member 90 to translate and/or rotate the vertebral member 90 into alignment.

In one embodiment as illustrated in FIGS. 8 and 9, the insertion process is performed percutaneously by the surgeon manipulating the handle 62 of the inserter 60 which remains on the exterior of the patient. In one embodiment, movement of the rod 50 through the patient P is performed using fluoroscopy imaging techniques.

In one embodiment, the windows 36 formed at the various anchors 20 by the extenders 30 are in the open orientation prior to and during insertion of the corrective rod 50. In one embodiment, the window 36 is moved to the closed orientation once the tip 51 has moved through the window. The reduction includes rotating the fitting 38 on the proximal end 32 of the extender 30. As best illustrated in FIGS. 4 and 5, rotation of the fitting 38 causes the sliding member 34 to move distally along the tubular element 33. This movement causes the contact edge 35 on the sliding member 34 to contact and move the corrective rod 50 distally towards the anchor 20. In one embodiment, the windows 36 are completely closed with the rod 50 being seated within the anchors 20. In another embodiment, the windows 36 may only be partially closed. In another embodiment, the windows 36 may remain in the open orientation until the rod 50 is positioned through each of the anchors 20.

In one embodiment, the corrective rod 50 is rotated at each spinal level as part of the insertion process of moving the tip 51 through each anchor 20. As illustrated in FIG. 8, the rod 50 may be originally inserted into the patient P while in a first rotational position. This first orientation may include the handle 62 being in a vertical orientation that is spaced away from the patient P. During the insertion, the rod 50 may ultimately end up in a different rotational position as illustrated in FIG. 9. The amount of rotation between the initial insertion and final position may vary depending upon the application. In one embodiment as illustrated in FIGS. 8 and 9, the amount of rotation is about 90 degrees. Other embodiments may include rotation of about 180 degrees.

In another embodiment, the corrective rod 50 remains substantially within the same rotational position during insertion into the patient. Once the rod 50 is positioned through each of the anchors 20, the rod 50 is rotated to apply the additional corrective force to the vertebral members 90 due to the curvature of the rod 50.

Figure 10A:
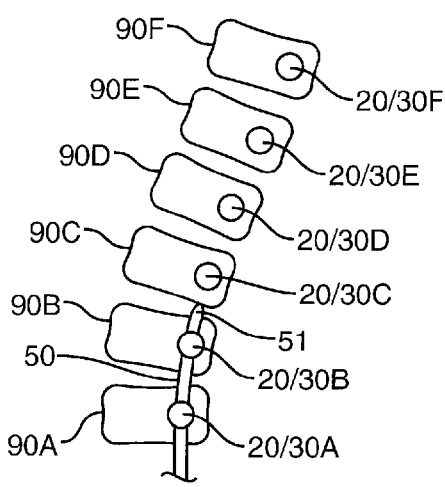
FIGS. 10A-10F are schematic views illustrating a method of sequentially treating vertebral members according to one embodiment.
Figure 10B:
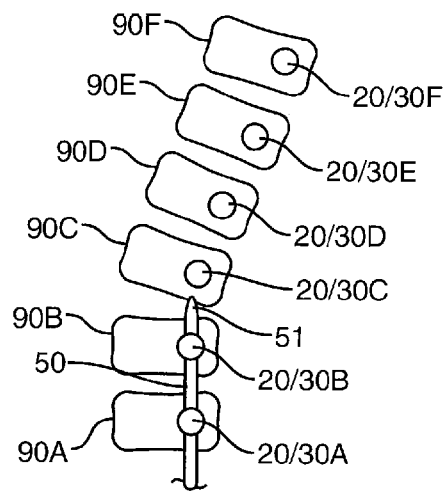

FIGS. 10A-10F illustrates the sequential steps of correcting the deformed spine. As illustrated in FIG. 10A, corrective rod 50 is initially inserted through the first window formed by anchor and extender 20/30A attached to the first vertebral member 90A. Once inserted, the corrective rod 50 is further manipulated to move the tip 51 through the second window formed by anchor and extender 20/30B attached to the second vertebral member 90B. The corrective rod 50 is rotated once it is positioned within the windows of anchor/extenders 20/30A, 20/30B, to align the first and second vertebral members 90A, 90B as illustrated in FIG. 10B.

Figure 10C:
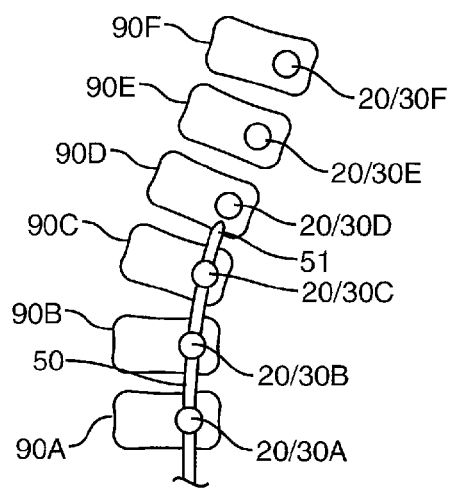
Figure 10D:
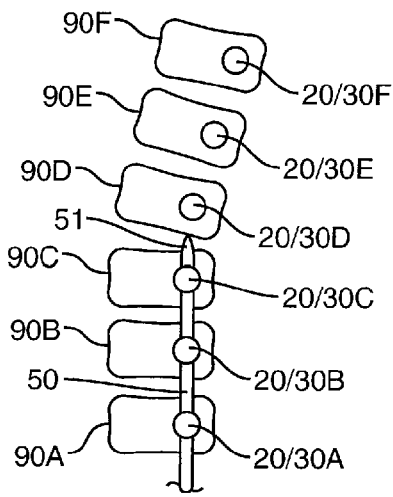

The corrective rod 50 is next inserted through a third window formed by anchor and extender 20/30C attached to a third vertebral member 90C as illustrated in FIG. 10C. After the corrective rod 50 is within the third window of anchor/extender 20/30C and prior to insertion into a subsequent window formed by anchor/extender 20/30D, the corrective rod 50 is again rotated to align the first three vertebral members 90A, 90B, 90C as illustrated in FIG. 10D.

Figure 10E:
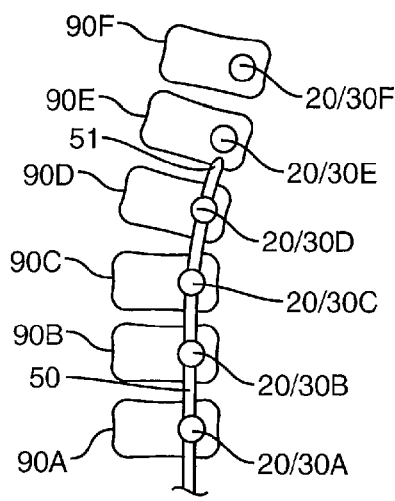
Figure 10F:
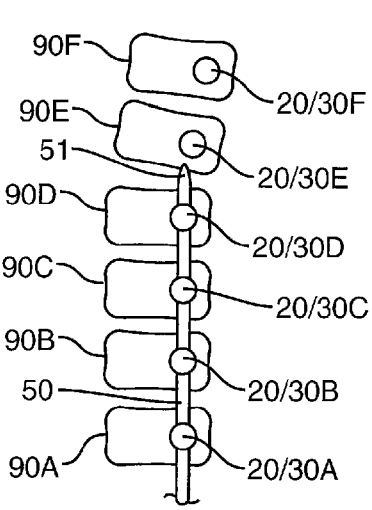

The corrective rod 50 is than moved in a manner to insert the tip 51 through the fourth window of anchor/extender 20/30D attached to the fourth vertebral member 90D as illustrated in FIG. 10E. Once inserted, the corrective rod 50 is rotated to align the first four vertebral members 90A, 90B, 90C, 90D as illustrated in FIG. 10F. This sequential process continues with the remaining vertebral member 90E, 90F of the deformed spine being individually aligned by moving the corrective rod 50 through the windows associated with anchor/extenders 20/30E and 20/30F and rotating the corrective rod 50.

The extenders 30 attached to the anchors 20 are also used during the sequential process to apply forces to the vertebral members 90. Once the corrective rod is inserted through the first two windows formed by anchors/extenders 20/30A and 20/30B as illustrated in FIG. 10A, the windows may be substantially closed. The closing action may force the corrective rod to seat within the anchors. The reduced window size also causes the rotational force of the corrective rod 50 to be applied to the vertebral members 90A, 90B. The windows remain open enough to allow for the corrective rod 50 to be inserted into the other subsequent windows.

The windows may be closed or opened sequentially at each vertebral member 90 prior to rotation of the corrective rod 50. As illustrated in FIG. 10C, window formed at anchor/extender 20/30C is closed prior to rotation as illustrated in FIG. 10D. Likewise, window formed at anchor/extender 20/30D is closed prior to rotation illustrated in FIG. 10F.

Figure 11:
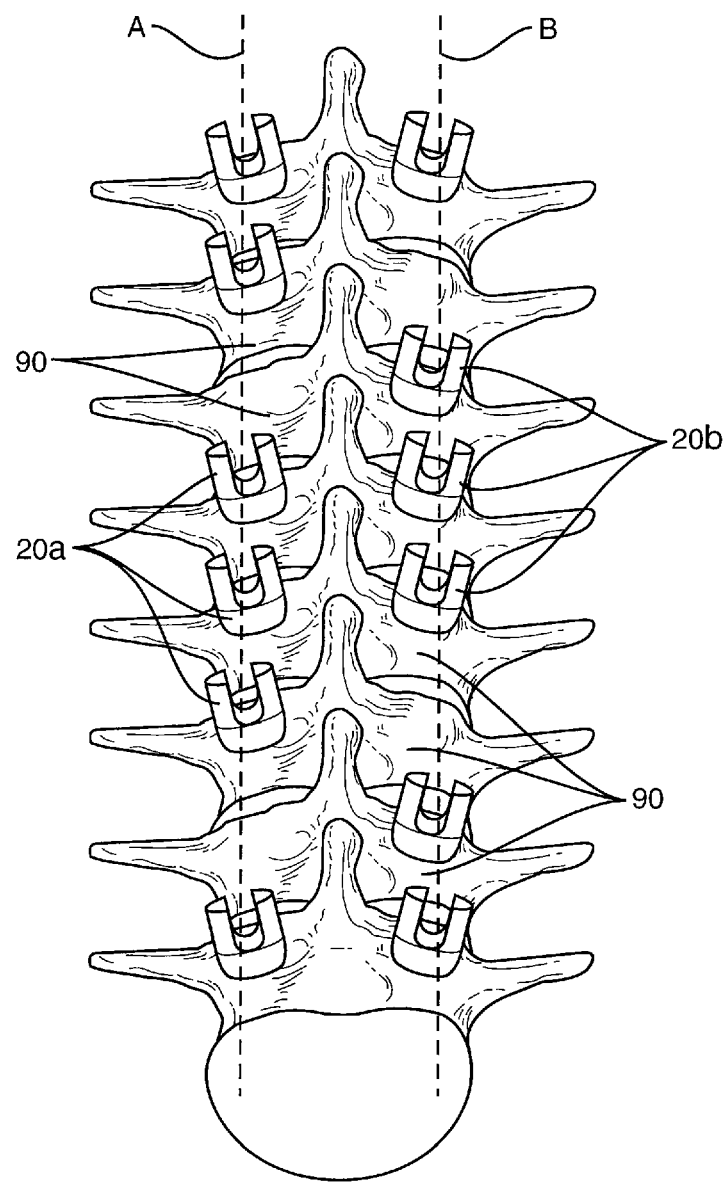
FIG. 11 is a schematic view of anchors attached to the vertebral members along a section of the spine according to one embodiment.

The corrective rod 50 aligns the vertebral members 90 as schematically illustrated in FIG. 11. For purposes of clarity, the corrective rod 50 and the extenders 30 are removed from this Figure.

With the corrective rod 50 remaining within one of the anchor rows A, B, a second rod 60 is inserted within the second row. In one embodiment, prior to insertion of the second rod 60, extenders 30 are attached to the anchors 20 of the second row. In one embodiment, attachment of the extenders 30 to the second row of anchors 20 may occur prior to insertion of the corrective rod 50. In another embodiment, the extenders 30 are attached after the corrective rod 50 has been inserted and alignment of the vertebral members 90.

The second rod 60 maintains the vertebral members 90 within their new alignment. The process of inserting the second rod 60 may be similar to insertion of the corrective rod 50. The surgeon percutaneously inserts the second rod 60 into the patient and moves the second rod 60 through each of the anchors 20. For anchors 20 with associated extenders 30, the windows 36 are reduced in size towards the closed orientation after insertion of the second rod 60.

Once the second rod 60 is positioned, set screws may be attached to the anchors 20 to maintain the position of the rod 60. In anchors 20 with extenders 30, the set screws may be inserted through the interior of the extenders 30. The set screws engage with threads on the anchors 20 and maintain the second rod 60 attached to the anchors 20. In one embodiment, the set screws may include threads that engage with the head portions of the bone anchors 20 via a driving tool to maintain the rod 60 in engagement with the anchors 20. In one embodiment, a driving tool is inserted through the interior of the extenders 30. The tool includes a drive shaft including a distal end portion that is positioned within a tool receiving recess in the set screw, and a handle for imparting rotational force onto the drive shaft.

In one embodiment, the corrective rod 50 remains within the patient after the surgical procedure. The corrective rod 50 maintains the alignment of the vertebral members 90.

Figure 12:
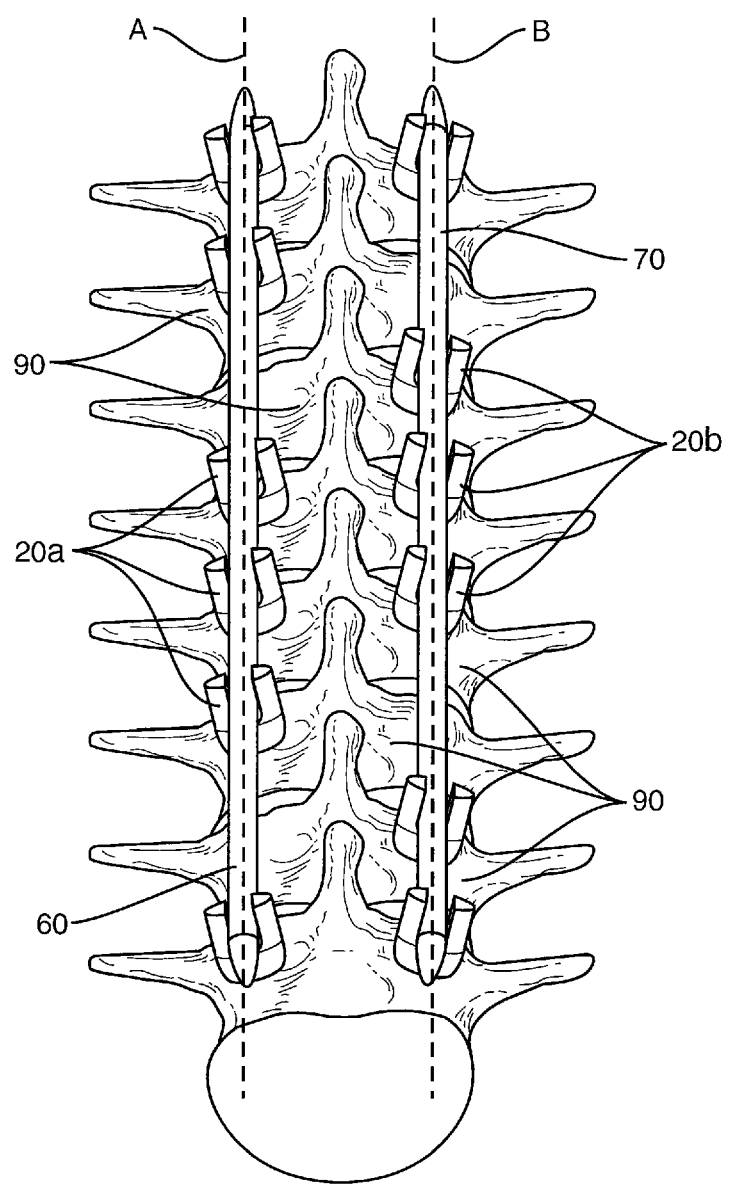
FIG. 12 is a schematic view of vertebral rods attached to anchors along a section of the spine according to one embodiment.

In another embodiment, once the second rod 60 is attached along one anchor row, the corrective rod 50 may be removed. Removal may initially require one or more of the windows 36 to be moved towards the open orientation. Removal requires the surgeon to manipulate the handle 62 and pull the corrective rod 50 from each anchor 20 and from the patient P. In one embodiment, a third rod 70 is then inserted to replace the corrective rod 50. Third rod 70 is shaped to maintain the vertebral members 90 in proper alignment. The insertion and attachment method is similar to that described above with reference to the second rod 60. FIG. 12 illustrates one embodiment with the second rod 60 inserted within the anchors 20a of row A, and the third rod 70 within the anchors 20b of row B.

In one embodiment as described above, the corrective rod 50 is rotated after initial insertion to provide an additional amount of corrective force to be applied to the vertebral members 90. In another embodiment, threading the corrective rod 50 through the windows 36 provides an adequate amount of corrective force and aligns the vertebral members 90. In this embodiment, the corrective rod 50 is not rotated to a second rotational position.

In the embodiment described above, extenders 30 are attached to one or more of the anchors 20. The extenders 30 may be attached to each of the anchors 20 along one or both anchor rows A, B, or along less than each anchor 20. In one embodiment, no extenders 30 are attached to the anchors 20 and the one or more rods are inserted directly into the receivers 23 in the anchors 20.

In the embodiments of FIGS. 11 and 12, two anchor rows A, B are attached to the vertebral members 90. In another embodiment, a single anchor row is attached to the vertebral members 90. In one embodiment with a single anchor row, the corrective rod 50 is removed after the vertebral members 90 are moved into alignment, and replaced with a second rod. In another embodiment with a single anchor row, the corrective rod 50 remains attached to the vertebral members 90 and within the patient.

In one embodiment, rods 60, 70 are attached to the vertebral members 90 to maintain the alignment. Various other members may be used to maintain the alignment of the vertebral members 90. The members may include but are not limited to a plate, bar, cable, tether, or other suitable elongate implant capable of maintaining the vertebral members 90 in the corrected alignment.

In one embodiment, the rods 50, 60, 70 are formed of a biocompatible material, such as, for example, stainless steel or titanium. However, other materials are also contemplated, including, for example, titanium alloys, metallic alloys such as chrome-cobalt, polymer based materials such as PEEK, composite materials, or combinations thereof. In one embodiment, one or more of rods 50, 60, 70 include an injectable construction that is inserted into the patient and afterwards filled with a hardening polymer.

Rods 60, 70 may be substantially straight within the plane illustrated in FIG. 11. In another embodiment, the rods 60, 70 are bent or contoured, either outside of the patient's body or in-situ, to more closely match the position, orientation and alignment of the vertebral members 90.

In the embodiment described above, the extenders 30 include sliding members 34 to adjust the size of the windows 36. In another embodiment, extenders 30 are cylindrical tubes that do not include sliding members 34. A distal end of the tubes may be threaded to engage with the anchors 20, and the interior be substantially open to insert a set screw.

The devices and methods may be used to treat various abnormal spinal curvatures such as scoliosis. The devices and methods may also be used to treat other spinal deformities including kyphotic deformities such as Scheurmann's kyphosis, fractures, congenital abnormalities, degenerative deformities, metabolic deformities, deformities caused by tumors, infections, trauma, and other abnormal spinal curvatures.

In one embodiment, the devices and methods are configured to reposition and/or realign the vertebral members 90 along one or more spatial planes toward their normal physiological position and orientation. The spinal deformity is reduced systematically in all three spatial planes of the spine, thereby tending to reduce surgical times and provide improved results. In one embodiment, the devices and methods provide three-dimensional reduction of a spinal deformity via a posterior surgical approach. However, it should be understood that other surgical approaches may be used, including, a lateral approach, an anterior approach, a posterolateral approach, an anterolateral approach, or any other surgical approach.

The anchors 20 described above are some embodiments that may be used in the present application. Other examples include spinal hooks configured for engagement about a portion of a vertebral member 90, bolts, pins, nails, clamps, staples and/or other types of bone anchor devices capable of being anchored in or to vertebral member 90. In one embodiment, anchors 20 include fixed angle screws.

In still other embodiments, bone anchors may allow the head portion to be selectively pivoted or rotated relative to the threaded shank portion along multiple planes or about multiple axes. In one such embodiment, the head portion includes a receptacle for receiving a spherical-shaped portion of a threaded shank therein to allow the head portion to pivot or rotate relative to the threaded shank portion. A locking member or crown may be compressed against the spherical-shaped portion via a set screw or another type of fastener to lock the head portion at a select angular orientation relative to the threaded shank portion. The use of multi-axial bone anchors may be beneficial for use in the lower lumbar region of the spinal, and particularly below the L4 vertebral member, where lordotic angles tend to be relatively high compared to other regions of the spinal column. Alternatively, in regions of the spine exhibiting relatively high intervertebral angles, the anchors 20 may include a fixed angle.

In one embodiment, the treatment of the deformity is performed percutaneously. In other embodiments, the treatment is performed with an open approach, semi-open approach, or a muscle-splitting approach.

Spatially relative terms such as "under", "below", "lower", "over", "upper", and the like, are used for ease of description to explain the positioning of one element relative to a second element. These terms are intended to encompass different orientations of the device in addition to different orientations than those depicted in the figures. Further, terms such as "first", "second", and the like, are also used to describe various elements, regions, sections, etc and are also not intended to be limiting. Like terms refer to like elements throughout the description.

As used herein, the terms "having", "containing", "including", "comprising" and the like are open ended terms that indicate the presence of stated elements or features, but do not preclude additional elements or features. The articles "a", "an" and "the" are intended to include the plural as well as the singular, unless the context clearly indicates otherwise.

The present invention may be carried out in other specific ways than those herein set forth without departing from the scope and essential characteristics of the invention. The present embodiments are, therefore, to be considered in all respects as illustrative and not restrictive, and all changes coming within the meaning and equivalency range of the appended claims are intended to be embraced therein.

What is claimed is:

1. A method of treating a patient with a spinal deformity comprising the steps of:
   inserting an elongated corrective member into the patient with the corrective member in a first rotational position;
   moving the corrective member through a first anchor attached to a first vertebral member;
   further inserting the corrective member into the patient and moving the corrective member through a second anchor attached to a second vertebral member and applying a first corrective force to move the second vertebral member relative to the first vertebral member;
   further inserting the corrective member into the patient and moving the corrective member through a third anchor attached to a third vertebral member and applying a second corrective force to move the third vertebral member relative to the first and second vertebral members; and
   rotating the corrective member from the first rotational position to a second rotational position after moving the corrective member through the third anchor to align the second vertebral member with the first vertebral member and align the third vertebral member with the first and second vertebral members,
   wherein the corrective member remains within the first rotational position as the corrective member moves through the anchors.

2. A method as recited in claim 1, wherein the corrective member is rotated about 90 degrees to rotate the corrective member from the first rotational position to the second rotational position.

3. A method as recited in claim 1, wherein the corrective member is rotated about 180 degrees to rotate the corrective member from the first rotational position to the second rotational position.

4. A method as recited in claim 1, further comprising:
   implanting the first anchor on a lateral side of a spinous process of the first vertebral member;
   implanting the second anchor on a lateral side of a spinous process of the second vertebral member; and
   implanting the third anchor on a lateral side of a spinous process of the third vertebral member.

5. A method as recited in claim 4, wherein implanting the anchors includes threading a shaft of each of the anchors into a respective one of the vertebral members.

6. A method as recited in claim 1, wherein the anchors each include a threaded shaft coupled with a head, the head comprising a pair of spaced apart arms defining a U-shaped implant cavity therebetween configured for disposal of the corrective member, the head being fixed to the shaft.

7. A method as recited in claim 1, wherein the anchors each include a threaded shaft coupled with a head, the head comprising a pair of spaced apart arms defining a U-shaped implant cavity therebetween configured for disposal of the corrective member, the head movable relative to the shaft in more than one plane.

8. A method as recited in claim 1, wherein the corrective member includes a pre-bent shape configured to apply specific corrective forces to each of the vertebral members.

9. A method as recited in claim 8, wherein the pre-bent shape is determined based upon flexibility of the spinal deformity prior to treatment.

10. A method as recited in claim 8, wherein the pre-bent shape includes bends in three dimensions.

11. A method as recited in claim 1, wherein:
    the method further comprises attaching the corrective member to an inserter comprising a handle; and
    the corrective member is moved through the anchors percutaneously by manipulating the handle which is positioned outside of the patient.

12. A method of treating a patient with a spinal deformity comprising the steps of:
    attaching an elongated corrective member to an inserter comprising a handle;
    inserting the corrective member into the patient with the corrective member in a first rotational position;
    moving the corrective member through a first anchor attached to a first vertebral member;
    further inserting the corrective member into the patient and moving the corrective member through a second anchor attached to a second vertebral member and applying a first corrective force to move the second vertebral member relative to the first vertebral member; and
    further inserting the corrective member into the patient and moving the corrective member through a third anchor attached to a third vertebral member and applying a second corrective force to move the third vertebral member relative to the first and second vertebral members; and
    rotating the corrective member from the first rotational position to a second rotational position after moving the corrective member through the third anchor to align the second vertebral member with the first vertebral member and align the third vertebral member with the first and second vertebral members,
    wherein the corrective member is moved through the anchors percutaneously by manipulating the handle which is positioned outside of the patient,
    wherein the anchors each include a threaded shaft coupled with a head, the head comprising a pair of spaced apart arms defining a U-shaped implant cavity therebetween configured for disposal of the corrective member, the head being moveable relative to the shaft in more than one plane, and
    wherein the corrective member remains within the first rotational position as the corrective member moves through the anchors.

13. A method of treating a patient with a spinal deformity comprising the steps of:
    inserting a corrective member into the patient with the corrective member in a first rotational position;
    moving the corrective member through a first anchor attached to a first vertebral member;
    moving the corrective member through a second anchor attached to a second vertebral member;
    moving the corrective member through a third anchor attached to a third vertebral member; and
    rotating the corrective member from the first rotational position to a second rotational position after moving the corrective member through the third anchor to align the second vertebral member with the first vertebral member and align the third vertebral member with the first and second vertebral members.

14. A method as recited in claim 13, wherein the corrective member remains within the first rotational position as the corrective member moves through the anchors.

15. A method as recited in claim 13, wherein:
- moving the corrective member through the second anchor comprises applying a first corrective force to move the second vertebral member relative to the first vertebral member; and
- moving the corrective member through the third anchor comprises applying a second corrective force to move the third vertebral member relative to the first and second vertebral members.

16. A method as recited in claim 13, wherein:
- the anchors each include a threaded shaft coupled with a head, the head comprising a pair of spaced apart arms defining a U-shaped implant cavity therebetween configured for disposal of the corrective member, the head being moveable relative to the shaft in more than one plane;
- the method further comprises attaching the corrective member to an inserter comprising a handle; and
- the corrective member is moved through the anchors percutaneously by manipulating the handle which is positioned outside of the patient.

17. A method as recited in claim 13, wherein the corrective member is rotated about 90 degrees to rotate the corrective member from the first rotational position to the second rotational position.

18. A method as recited in claim 13, wherein the corrective member is rotated about 180 degrees to rotate the corrective member from the first rotational position to the second rotational position.

* * * * *